United States Patent [19]

Ho et al.

[11] 4,329,508

[45] May 11, 1982

[54] PROCESS FOR MAKING ALKYL CYCLOPENTENONES

[75] Inventors: T. L. Ho, Jacksonville; Shing-Hou Liu, Atlantic Beach, both of Fla.

[73] Assignee: SCM Corporation, New York, N.Y.

[21] Appl. No.: 192,083

[22] Filed: Sep. 29, 1980

[51] Int. Cl.$^3$ ............................................. C07C 45/52
[52] U.S. Cl. .................................... 568/361; 568/838; 560/122; 560/121; 549/525; 549/546
[58] Field of Search .............................. 568/361, 838; 260/348.25; 560/122, 121

[56] References Cited

U.S. PATENT DOCUMENTS 3,775,492  11/1973  Kierstead et al. ................... 568/838
3,911,026  10/1975  Kierstead et al. ................... 568/838
4,048,242   9/1977  Lauer et al. ......................... 585/271

OTHER PUBLICATIONS

Organic Synthesis, Col. vol. 5, pp. 326–328, 414–418, (1980).
Piancatelli et al., Tetrahedren, vol. 35(1), pp. 135–138, (1979).
Synthesis, 1980, pp. 118–119.
House, "Modern Synthetic Reactions", pp. 298–299, (1972), Benjamin Inc.
Norman, Principles of Organic Synthesis", Chapman & Hall, pp. 568–569, (1968).

*Primary Examiner*—Natalie Trousof
*Assistant Examiner*—James H. Reamer
*Attorney, Agent, or Firm*—Robert A. Sturges; Merton H. Douthitt

[57] ABSTRACT

A process for making mixed 2- and 3-$C_1$–$C_{10}$ alkyl-2-cyclopenten-1-ones from a corresponding alkylcyclopentadiene by epoxidation to the oxiranes, hydrolysis to the diols, dehydration of the diols and rearrangement of the resulting mixed alkylcyclopentenones. The resulting product can be used to make methylcyclopentenolone, a synthetic maple flavor.

20 Claims, No Drawings

PROCESS FOR MAKING ALKYL CYCLOPENTENONES

The present invention relates to a method for making alkyl cyclopentenones from an alkyl cyclopentadiene. A particularly useful alkyl cyclopentenone is methyl cyclopentenone prepared from methyl cyclopentadiene. A convenient source of methyl cyclopentadiene is from depolymerization of the readily available methyl cyclopentadiene dimer. The starting material can be obtained by thermally cracking the latter at about 180°–200° C. The products of the present process are useful in many syntheses, such as the production of a maple flavor ingredient, steroid syntheses, etc. The derivative wherein the alkyl group is iso-amyl (2 iso-amylcyclopentenone) is also known as nor-iso-jasmone having a preferable odor with respect to jasmine similarity.

BACKGROUND OF THE INVENTION AND PRIOR ART

It is known to crack dicyclopentadiene to the monomer (U.S. Pat. No. 4,048,242, for example). It is also known to produce dihydroxycyclopentene (cyclopentenediol) by reacting the hydrocarbon with peroxyacetic acid followed by hydrolysis in cold water to produce the diol (Organic Synthesis, Coll. Vol. V., Pages 414–418). 2-cyclopentene-1-one is produced from this diol by treatment with a catalytic amount of a sulfonic acid, e.g., p-toluene sulfonic acid. (ibid. Pages 326–328). 2-alkylcyclopentadienes are also conveniently prepared by alkylation of cyclopentadienide salts of alkali metals or halomagnesium.

Cyclopenteneone is not useful to produce methylcyclopentenolone (synthetic maple flavor). 2-Methyl-2-cyclopenten-1-one is a useful starting material for the production of steroids (Synthesis (1980) pages 118–119). This recent reference lists 18 methods of making 2-methyl-2-cyclopenten-1-one ranging in yield from 16% to 90%. The authors recommend reduction of 3-isobutyloxy-2-methyl-2-cyclopenten-1-one derived from 2-methyl cyclopentane-1,3-dione with lithium aluminum hydride or diisobutylaluminum hydride followed by stirring in a mixture of ether and $MnO_2$ to obtain pure 2-methyl-2-cyclopenten-1-one in a 62% yield, as being "the most convenient to perform in the laboratory, at least as efficient as other methods, and it adds another practical variant to currently known synthetic approaches to this compound."

The present invention provides an efficient, commercially suitable method for making a methyl product of somewhat lower purity (a mixture of the 2- and 3-isomers) in a combined yield of about 85% (78% 2-methyl-2-cyclopenten-1-one).

It has been found that the alkyl substituent has a profound effect on the relative reactivity of the double bonds in the alkylcyclopentadiene. The double bond adjacent the alkyl substituent is more highly reactive to peracids producing therefrom larger portions of the epoxides (a) and (b) below. This effect is reflected in the ultimate ratio of 2- and 3- alkylcyclopentenones. A surprisingly high selectivity in this respect was obtained.

BRIEF STATEMENT OF THE INVENTION

Briefly stated, the present invention is in a process for making alkylcyclopentenones from alkylcyclopentadiene. The alkylcyclopentadiene is reacted with a peroxy acid, e.g., $R'CO_3H$, (wherein $R'$ is a $C_1$–$C_{10}$ hydrocarbyl group) to form epoxides. The epoxides are hydrolyzed in aqueous medium to the diols. The diols are then dehydrated and rearranged to yield a ketone mixture predominately comprising 2-alkyl-2-cyclopenten-1-one.

For convenience in the initial portion of this discussion reference will be had to the methyl substituted materials.

DETAILED DESCRIPTION OF THE INVENTION AND SPECIFIC EXAMPLES

As indicated above, thermal cracking of readily available methylcyclopentadiene dimer yields a mixture of mainly two monomers as follows:

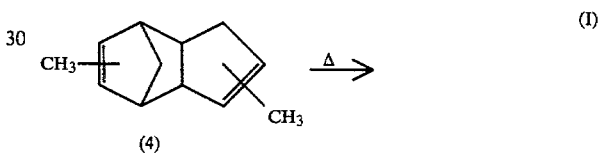

(I)

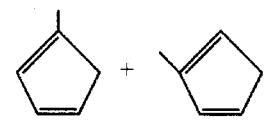

(5)

The monomer mixture (5) is then reacted with a peroxy acid to yield a mixture of four epoxides. The peroxyacid has the general formula $R'CO_3H$, where $R'$ is a hydrocarbyl group as above defined, including alkyl and aryl substituted lower alkyl, e.g., peroxyacetic acid, peroxybenzoic acid.

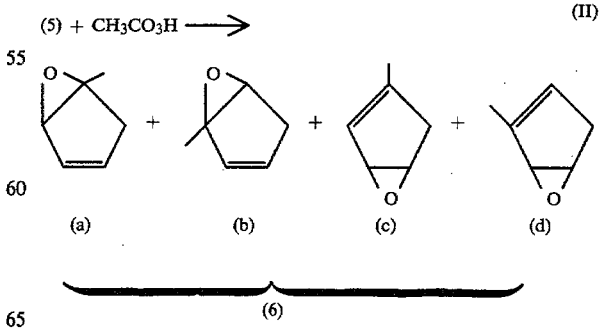

(II)

The mixture of epoxides (6) is then hydrolyzed with water to form a complex mixture of diols:

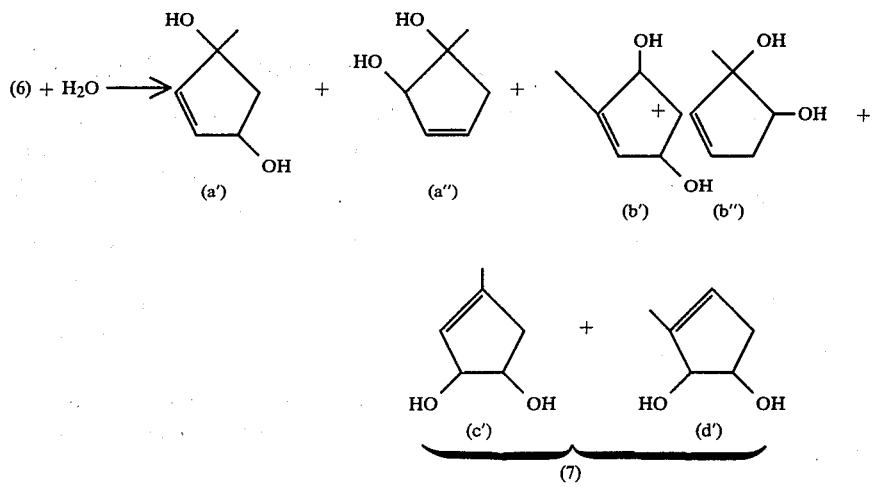

The resulting complex mixture of diols (7) is then dehydrated by treatment with an acid, such as p-toluene sulfonic acid:

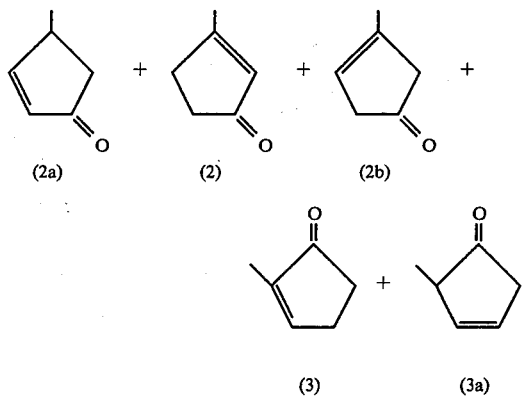

Thereafter, (2a), (2b) and (3a) are rearranged by contact with neutral alumina, or with acid or base, respectively, to (2) and (3) and the mixture eluted with an oxygen containing solvent, e.g., an alkyl ether (Et₂O), to a mixture of (2) and (3), and this mixture then recovered as product. (See procedure in Tetrahedron, Vol. 35, Pages 135-138 (1979), the disclosure of which is incorporated herein by reference thereto). This mixture may be refined, as for example, by fractional vacuum distillation.

Referring now to equations (II) and (III) above, the hydration of the epoxides formed by equation (II) proceeds in (III) in the following manner:

(a)→a′, a″

(b)→b′, b″

(c)→a′, c′

(d)→b′, d′

The products (a) and (b) are the major products of the epoxidation reaction (II). Actually, more (b) is produced than (a). As a first approximation, (c) and (d) can be ignored. Thus, eventually, most of the 2-, and 3-methyl-2-cyclopenten-1-ones would come from:

a′→3-isomer a″→2-isomer b′→2-and 3-isomers b″→2-isomer

Thus, it can now be seen that the 2-isomer will predominate. The extent to which it does predominate is indeed surprising as will be illustrated in the following examples: From a knowledge of the hydration of 3,4-epoxycyclopentene, one would expect mainly the 1,4-diol (Org. Syn. Coll. Vol. 5., Pages 415-416). Thus, the presence of the alkyl group apparently causes the reverse situation to obtain, leading, therefore, to a predominance of the 1,2-diol.

EXAMPLE I

Methylcyclopentenediols

Methylcyclopentadiene dimer was pyrolyzed (pot temp. 180° C.) in a flask and the monomers (b.p. 75° C.) were directly distilled into a cold receiver (dry ice-isopropanol bath). A solution of the monomer (62.5 g) in methylene chloride (500 ml) was then placed in a flask together with sodium carbonate (106 g) and stirred mechanically while the peracetic acid (40%, 76 g, pretreated with 2 g of sodium acetate) was added during 15 min., the temperature being maintained between 16°-20° C. by intermittant cooling. The reaction mixture was filtered by suction and the filtrate was mixed with water (10 ml). Methylene chloride was removed by distillation with a rotary evaporator to give the diols which were used without further purification.

EXAMPLE II

Methylcyclopentenones

The diol mixture obtained in Example I was mixed with p-toluenesulfonic acid monohydrate (0.5 g) and subjected to short-path distillation at 45° C./13 mm Hg. In the course of 1 hr. a yellow liquid was collected weighing 18.5 g. The distillate was dissolved in methylene chloride (100 ml) and washed with sodium bicarbonate solution, dried, and evaporated to give 14.0 g of product containing 2-methyl-2-cyclopentenone (59.1%), 3-methyl-2-cyclopentenone (2.98%) and two other isomers (16.8% and 10.8%, respectively). The latter two isomers were converted on contact with neutral alumina, by the process disclosed in Tetrahedron, supra., into the desired compounds and thereby a mixture of mainly 2-methyl-2-cyclo-pentenone (78.4%) and 3-methyl-2-cyclopentenone (8.2%) was obtained.

Both the products (2) and (3) of equation (IV) are useful in the synthesis of methylcyclopentenolone by epoxidation and acid catalyzed rearrangement. Thus, the present process represents a convenient method to get to the maple flavor ingredient.

EXAMPLE III

Pentylcyclopentadiene

To a solution of sodium cyclopentadienide (71 mmole, 1.89 M in THF) in 20 ml of THF was added 10 ml of hexamethylphosphoramide. The solution was cooled to $-55°$ C. and 1-bromopentane (10.5 g. 70 mmole) was added dropwise with stirring over a period of 30 min. After the addition was completed, the reaction mixture was stirred at $-30°-40°$ C. for 30 minutes and at autogeneous temperature for 30 minutes, then poured into cold water and extracted with pentane, $(3 \times 80$ ml). The pentane extracts were combined, washed with water $(3 \times 100$ ml) dried over anhydrous sodium sulfate, filtered and concentrated in a rotary evaporator (water bath temperature 20° C.). The residue was distilled to give 8.1 g (85%) of pentylcyclopentadiene, b.p. 52°/8 mm Hg.

EXAMPLE IV

2 and 3-Pentyl-cyclopentenones

In a 250 ml three-necked flask was placed 7.9 g (58 mmole) of freshly distilled pentylcyclopentadiene, 15.6 g (147 mmole) of anhydrous sodium carbonate, and 100 ml of methylene chloride. A solution of 0.3 g of sodium acetate in 11 g of 40% peracetic acid (0.58 mmole) was added with stirring over a period of 10 min. The temperature was maintained at 0°-5° C., was then gradually warmed up to room temperature. When potassium iodide-starch test indicated the reaction was complete, solid was removed by suction filtration. The filtrate was stirred with 3 ml of water for 2 hours and methylene chloride was removed by rotary evaporation.

The residue consisting of a mixture of diols was mixed with 100 mg of p-toluenesulfonic acid monohydrate and was distilled under reduced pressure to give 2.7 g (31%) bp. 85%/2 mm Hg. of 2- and 3-pentyl-2-cyclopentenones. Nuclear Magnetic Resonance spectrum and vapor phase Chromatography showed the ratio of the pentylcyclopentenones to be 3.6 to 1.

2-pentyl-2-cyclopentenone is a precursor of dihydrojasmone and methyl dihydrojasmonate. Hydrogenation of 2-pentyl-2-cyclopentenone yields 2-pentylcyclopentanone, a commercially available flavorant.

EXAMPLE V

Ethyl cyclopentadiene, n-propyl cyclopentadiene, iso-propylcyclopentadiene, n-butyl cyclopentadiene, t-butyl cyclopentadiene, n-hexyl cyclopentadiene (2-ethyl hexyl) cyclopentadiene, and the like may be prepared following the procedure set forth in Example III.

EXAMPLE VI

2-, and 3-alkyl cyclopentenones corresponding to the alkyl cyclopentadienes of Example V may be prepared following the procedure of Example IV. The products are all useful as flavorants. The 2-, and 3-ethyl-2-cyclopentenones are readily converted to the maple flavorant ethylcyclopentenolone, for example.

The alkyl substituent may also contain oxygen and have the general formula $-(CH_2)_n COOR''$ where $R''$ is $C_1-C_6$ hydrocarbyl and n is an integer from 1–9. Thus, the 6-carboalkoxyhexyls [$-(CH_2)_6 COOR''$, where $R''$ is as defined above] are especially useful in the preparation of prostaglandins. The $C_1-C_{10}$ alkyl cyclopentenones are useful not only as flavorants the manners of use of which are well known, but also as intermediates in the preparation of many useful and valuable chemicals.

What is claimed is:

1. A process for producing substituted 2-cyclopenten-1-ones from a corresponding substituted cyclopentadiene which comprises the steps of forming a mixture of epoxy substituted cyclopentenes by reaction with a peroxyacid, hydrolyzing said mixture of epoxy substituted cyclopentenes with water to form a mixture of dihydroxy-substituted cyclopentenes and dehydrating said dihydroxy substituted cyclopentenes in the presence of an acid to form a mixture containing 2-, and 3-substituted-2-cyclopenten-1-ones, and wherein the substituted group is selected from $C_1-C_{10}$ alkyl groups and substituted $C_1-C_{10}$ alkyl groups having the general formula:

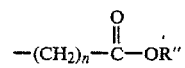

wherein $R''$ is a $C_1-C_{10}$ alkyl group and n is an integer from 1-9.

2. A process as defined in claim 1 wherein the $C_1-C_{10}$ alkyl group is methyl.

3. A process as defined in claim 1 wherein the $C_1-C_{10}$ alkyl group is ethyl.

4. A process as defined in claim 1 wherein the $C_1-C_{10}$ alkyl group is a propyl group.

5. A process as defined in claim 1 wherein the $C_1-C_{10}$ alkyl group is a butyl group.

6. A process as defined in claim 1 wherein the $C_1-C_{10}$ alkyl group is an amyl group.

7. A process as defined in claim 6 wherein the amyl group is isoamyl.

8. A process as defined in claim 1 wherein the substituent group is a substituted alkyl group and has the formula:

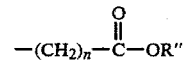

wherein $R''$ is a $C_1-C_6$ alkyl group and n is an integer from 1 to 9.

9. A process as defined in claim 8 wherein n is 6.

10. A process as defined in claim 9 wherein $R''$ is methyl.

11. A process as defined in claim 1 wherein the peroxyacid has the general formula $R'CO_3H$ wherein $R'$ is a hydrocarbyl group containing from 1 to 10 carbon atoms.

12. A process as defined in claim 11 wherein the peroxyacid is peracetic acid.

13. A process as defined in claim 11 wherein the peroxyacid is peroxybenzoic acid.

14. A process as defined in claim 2 wherein the peroxyacid is peracetic acid.

15. A process as defined in claim 1 wherein the acid used to promote dehydration of the dihydroxyalkyl cyclopentenes is p-toluene sulphonic acid.

16. A process as defined in claim 1 further characterized by the step of rearranging the resulting ketones to enhance the yield of 2- and 3-alkyl-2-cyclopenten-1-ones.

17. A process as defined in claim 16 wherein the rearrangement is carried out by adsorption of the mixture containing 2-, and 3-alkyl-2-cyclopenten-1-ones on alumina followed by elution with a dialkyl ether.

18. A process for producing methyl-2-cyclo-pentene-1-ones from methyl cyclopentadiene which comprises the steps of forming a mixture of epoxymethylcyclopentenes by reaction with peracetic acid, hydrolyzing said mixture of epoxymethylcyclopentenes with water to form a mixture of dihydroxymethylcyclopentenes, and dehydrating said dihydroxymethylcyclopentenes in the presence of an acid to form a mixture containing 2-, and 3-methyl-2-cyclopenten-1-ones.

19. A process for producing pentyl-2-cyclopenten-1-ones from pentylcyclopentadiene which comprises the steps of forming a mixture of epoxypentylcyclopentenes by reaction with a peracetic acid, hydrolyzing said mixture of epoxypentylcyclopentenes with water to form a mixture of dihydroxypentylcyclopentenes, and dehydrating said dihydroxypentylcyclopentenes in the presence of an acid to form a mixture containing 2-, and 3-pentyl-2-cyclopenten-1-ones.

20. A process as defined in claim 19 wherein the pentyl group is isoamyl.

* * * * *